United States Patent [19]
Hu et al.

[11] Patent Number: 5,935,820
[45] Date of Patent: Aug. 10, 1999

[54] POLYNUCLEOTIDES ENCODING VASCULAR ENDOTHELIAL GROWTH FACTOR 2

[75] Inventors: Jing-Shan Hu, Sunnyvale, Calif.; Craig A. Rosen, Laytonsville, Md.; Liang Cao, South Horizon, The Hong Kong Special Administrative Region of the People's Republic of China

[73] Assignee: Human Genome Science, Inc., Rockville, Md.

[21] Appl. No.: 08/824,996

[22] Filed: Mar. 27, 1997

Related U.S. Application Data

[62] Division of application No. 08/207,550, Mar. 8, 1994, abandoned.

[51] Int. Cl.$^6$ ............................ C12N 15/18; C12N 15/63; C12N 1/21; C12N 5/00
[52] U.S. Cl. ................. 435/69.4; 435/70.1; 435/325; 435/320.1; 435/243; 536/23.4; 536/23.51; 530/399
[58] Field of Search .................................... 435/69.4, 325, 435/243, 320.1, 70.1; 530/399; 536/23.51, 23.4

[56] References Cited

U.S. PATENT DOCUMENTS

| | | | |
|---|---|---|---|
| 5,073,492 | 12/1991 | Chen et al. | 435/240.2 |
| 5,219,739 | 6/1993 | Tischer et al. | 435/69.4 |
| 5,326,695 | 7/1994 | Andersson et al. | 435/70.1 |

FOREIGN PATENT DOCUMENTS

| | | |
|---|---|---|
| 0476983 | 3/1992 | European Pat. Off. . |
| 0506477 | 9/1992 | European Pat. Off. . |
| 9705250 | 2/1997 | WIPO . |
| 9709427 | 3/1997 | WIPO . |
| 9717442 | 5/1997 | WIPO . |

OTHER PUBLICATIONS

Eichmann, A., et al., Development 125(4):743–752 (1998).
George et al. Macromolecular Seq. and Syn. Selected Meth & Applic pp. 127–149, 1998.
U.S. application No. 08/340011, filed Nov. 1994.
U.S. application No. 08/510133, filed Aug. 1995.
U.S. application No. 08/585895, filed Jan. 1996.
U.S. application No. 08/601132, filed Feb. 1996.
U.S. application No. 08/671573, filed Jun. 1996.
U.S. provisional application No. 60/03491, filed Sep. 1995.
U.S. application No. 08/8554374, filed Nov. 1995.
Pajusola, K., et al., Cancer Research. 52:5738–5743 (1992).
Pajusola, K., et al., Oncogene 8:2931–2937 (1993).
Tischer, et al., Biochemical and Biophysical Research Communications 165(3):1198–1206 (1989).
Leung, D.W., et al., Science 246:1306–1309 (1989).
Breier, G., et al., Development 114:521–532 (1992).
Ferrara, et al., Journal of Cellular Biochemistry 47:211–218 (1991).

*Primary Examiner*—John Ulm
*Assistant Examiner*—Christine Saoud
*Attorney, Agent, or Firm*—Human Genome Sciences Inc

[57] ABSTRACT

The present invention relates to polynucleotides encoding a novel human protein called Vascular Endothelial Growth Factor 2, or VEGF-2, as well as mature forms, proproteins, and fragments of VEGF-2. Also provided are vectors, host cells, and recombinant methods for producing VEGF-2. The invention further relates to polynucleotides that hybridize to polynucleotides of the present invention.

116 Claims, 10 Drawing Sheets

```
  1   CGAGGCCACGGCTTATGCAAGCAAAGATCTGGAGGAGCAGTTACGGTCTGTGTCCAGTGT
      ------------------------------------------------------------
                                M  T  V  L  Y  P  E  Y  W  K  M  Y  K  C  Q  L  R

71   AGATGAACTCATGACTGTACTCTACCCAGAATATTGGAAAATGTACAAGTGTCAGCTAAG
      ------------------------------------------------------------
      M  T  V  L  Y  P  E  Y  W  K  M  Y  K  C  Q  L  R

121   GAAAGGAGGCTGGCAACATAACAGAGAACAGGCCAACCTCAACTCAAGGACAGAGAAGAC
      ------------------------------------------------------------
       K  G  G  W  Q  H  N  R  E  Q  A  N  L  N  S  R  T  E  E  T

181   TATAAAATTTGCTGCAGCACATTATAATACAGAGATCTTGAAAAGTATTGATAATGAGTG
      ------------------------------------------------------------
       I  K  F  A  A  A  H  Y  N  T  E  I  L  K  S  I  D  N  E  W

241   GAGAAAGACTCAATGCCATGCCACGGGAGGTGTGTATAGATGTGGGGAAGGAGTTTGGAGT
      ------------------------------------------------------------
       R  K  T  Q  C  M  P  R  E  V  C  I  D  V  G  K  E  F  G  V

301   CGCGACAAACACCTTCTTTAAACCTCCATGTGTCCGTCTACAGATGTGGGGGTTGCTG
      ------------------------------------------------------------
       A  T  N  T  F  F  K  P  P  C  V  S  V  Y  R  C  G  G  C
```

FIG. 1A

```
361  CAATAGTGAGGGCTGCAGTGCATGAACACCAGCACGAGCTACCTCAGCAAGACGTTATT
      N  S  E  G  L  Q  C  M  N  T  S  T  S  Y  L  S  K  T  L  F

421  TGAAATTACAGTGCCTCTCTCTCAAGGCCCAAACCAGTAACAATCAGTTTGCCAATCA
      E  I  T  V  P  L  S  Q  G  P  K  P  V  T  I  S  F  A  N  H

481  CACTTCCTGCCGATGCATGTCTAAACTGGATGTTTACAGACAAGTTCATTCCATTATTAG
      T  S  C  R  C  M  S  K  L  D  V  Y  R  Q  V  H  S  I  I  R

541  ACGTTCCCTGCCAGCAACACTACCACAGTGTCAGGCAGCGAACAAGACCTGCCCCACCAA
      R  S  L  P  A  T  L  P  Q  C  Q  A  A  N  K  T  C  P  T  N

601  TTACATGTGGAATAATCACATCTGCAGATGCCTGGCTCAGGAAGATTTATGTTTTCCTC
      Y  M  W  N  N  H  I  C  R  C  L  A  Q  E  D  F  M  F  S  S

661  GGATGCTGGAGATGACTCAACAGATGGATTCCATGACATCTGTGGACCAAACAAGGAGCT
      D  A  G  D  D  S  T  D  G  F  H  D  I  C  G  P  N  K  E  L
```

FIG. 1B

```
 721  GGATGAAGAGACCTGTCAGTGTGTCTGCAGAGCGGGGCTTCGGCCTGCCAGCTGTGGACC
       D  E  E  T  C  Q  C  V  C  R  A  G  L  R  P  A  S  C  G  P

781  CCACAAAGAACTAGACAGAAACTCATGCCAGTGTGTCTGTAAAAACAAACTCTTCCCCAG
       H  K  E  L  D  R  N  S  C  Q  C  V  C  K  N  K  L  F  P  S

841  CCAATGTGGGGCCAACCGAGAATTTGATGAAAACACATGCCAGTGTGTATGTAAAGAAC
       Q  C  G  A  N  R  E  F  D  E  N  T  C  Q  C  V  C  K  R  T

901  CTGCCCCAGAAATCAACCCCTAAATCCTGGAAAATGTGCCTGTGAATGTACAGAAGTCC
       C  P  R  N  Q  P  L  N  P  G  K  C  A  C  E  C  T  E  S  P

961  ACAGAAATGCTTGTTAAAAGGAAAAAGAAGTTCCACCAAACATGCAGCTGTTACAGACG
       Q  K  C  L  L  K  G  K  K  F  H  H  Q  T  C  S  C  Y  R  R

1021  GCCATGTACGAACCGCCAGAAGGCTTGTGAGCCAGGATTTTCATATAGTGAAGAAGTGTG
       P  C  T  N  R  Q  K  A  C  E  P  G  F  S  Y  S  E  E  V  C
```

FIG. 1C

```
1081  TCGTTGTGTGTCCCTTCATATTGGCAAAGACCACACAAATGAGCTAAGATTGTACTGTTTCCA
      ----+----+----+----+----+----+----+----+----+----+----+----+
       R  C  V  P  S  Y  W  Q  R  P  Q  M  S

1141  GTTCATCGATTTTCTATTATGGAAAACTGTGTTGCCACAGTAGAACTGTCTGTGAACAGA
      ----+----+----+----+----+----+----+----+----+----+----+----+

1201  GAGACCCTGTGGGTCCATGCTAACAAAGACAAAAGTCTGTCTTTCCTGAACCATGTGGA
      ----+----+----+----+----+----+----+----+----+----+----+----+

1261  TAACTTTACAGAAATGGACTGGAGCTCATCTGCAAAAGGCCTCTTGTAAAGACTGGTTTT
      ----+----+----+----+----+----+----+----+----+----+----+----+

1321  CTGCCAATGACCAAACAGCCAAGATTTCCCTCTTGTGATTTCTTTAAAAGAATGACTATA
      ----+----+----+----+----+----+----+----+----+----+----+----+

1381  TAATTTATTCCACTAAAAATATGTTTCTGCATTCATTTTTATAGCAACAACAATTGGT
      ----+----+----+----+----+----+----+----+----+----+----+----+

1441  AAAACTCACTGTGATCAATATTTTTATATCATGCAAAATATGTTTAAAATAAATGAAAA
      ----+----+----+----+----+----+----+----+----+----+----+----+

1501  TTGTATTATAAAAAAAAAAAAAAA
      ----+----+----+
```

FIG.1D

```
       1                                                           50
Pdgfa  .MRTLACLLL LGCGYLAHVL AEEAEIPREV IERLARSQIH SIRDLQRLLE
Pdgfb  MNRCWA.LFL SLCCYLRLVS AEGDPIPEEL YEMLSDHSIR SFDDLQRLLH
 Vegf  ......MNFLL SWVHWSLALL LY................ .LHHAKWSQA
Vegf2  .......MTV LYPEYWKMYK CQ................. .LRKGGWQHN 51                                                         100
Pdgfa  IDSVGSEDSL DTSLRAHGVH ATKHVPEKRP LPIRRKRSI. ......EEAVP
Pdgfb  GDP.GEEDGA ELDLNMTRSH SGGELES... .LARGRRSLG SLTIAEPAMI
 Vegf  APMAE..... .......GGGQ NHHEVVKFMD .VYQR.... ..........
Vegf2  REQANLNSRT EETIKFAAAH YNTEILKSID NEWRK..... ..........

101                                                        150
Pdgfa  AVCKTRTVIY EIPRSQVDPT SANFLIWPPC VEVKRCTGCC NTSSVKCQPS
Pdgfb  AECKTRTEVF EISRRLIDRT NANFLVWPPC VEVQRCSGCC NNRNVQCRPT
 Vegf  SYCHPIETLV DIFQEYPDEI ..EYIFKPSC VPLMRCGGCC NDEGLECVPT
Vegf2  TQCMPREVCI DVGKEFGVAT ..NTFFKPPC VSVYRCGGCC NSEGLQCMNT 151                                                        200
Pdgfa  RVHHRSVKVA KVEYVRKKPK LKEVQVRLEE HLECAC.... AT........
Pdgfb  QVQLRPVQVR KIEIVRKKPI FKKATVLED HLACKC.... ETVAAARPVT
 Vegf  EESNITMQIM RIK.PH..QG QHIGEMSFLQ HNKCECRPKK DRARQEKKSV
Vegf2  STSYLSKTLF EIT.VPLSQG PKPVTISFAN HTSCRCMSKL DVYRQVHSII
```

FIG. 2A

```
       201
Pdgfa  ...TSLNPD YREEDTDVR. ........ .......... ..........         250
Pdgfb  RSPGGSQEQR AKTPQTRVTI RTVRVRRPPK GKHRKFKHTH DKTALKETLG
Vegf   RGK....... .GKGQKRKRK KSRYKSWSVY VGARCCLMPW SLPGPHP...
Vegf2  RRSLPATLPQ CQAANKTCPT NYMWNNHICR CLAQEDFMFS SDAGDDSTDG 251
Pdgfa  .......... .......... .......... .......... ..........         300
Pdgfb  A......... .......... .......... .......... ..........
Vegf   ...CGP.... .......... .......... .......... ..........
Vegf2  FHDICGPNKE LDEETCQCVC RAGLRPASCG PHKEL...DR NSCQCVCKNT 301
Pdgfa  .......... .......... .......... .......... ..........         350
Pdgfb  .......... .......... .......... .......... ..........
Vegf   ..DSRCKARQ LELNERTCRC DKPRR..... .......... ..........
Vegf2  LFPSQCGANR .EFDENTCQC VCKRTCPRNQ PLNPGKCACE CTESPQKCLL 351
Pdgfa  .......... .......... .......... .......... ....            398
Pdgfb  .......... .......... .......... .......... ....
Vegf   .......... .......... .......... .......... ....
Vegf2  KGKKFHHQTC SCYRRPCTNR QKACEPGFSY SEEVCRCVPS YWQRPQMS
```

FIG.2B

PERCENTAGE (%) OF AMINO ACID IDENTITIES BETWEEN EACH PAIR OF GENES IS SHOWN IN THE FOLLWING TABLE

| | PDGFα | PDGFβ | VEGF | VEGF2 |
|---|---|---|---|---|
| PDGFα | | | | |
| PDGFβ | 48.0 | | | |
| VEGF | 20.7 | 22.7 | | |
| VEGF2 | 23.5 | 22.4 | 30.0 | |

FIG.3

Expression of VEGF2 mRNA in human adult tissues.

Lane 1: 14-C and rainbow M.W. marker
Lane 2: FGF control
Lane 3: VEGF2 (M13-reverse $ forward primers)
Lane 4: VEGF2 (M13-reverse & VEGF-F4 primers)
Lane 5: VEGF2 (M13-reverse & VEGF-F5 primers)

POLYNUCLEOTIDES ENCODING VASCULAR ENDOTHELIAL GROWTH FACTOR 2

This is a Division of application Ser. No. 08/207,550, filed Mar. 8, 1994, now abandoned.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a human vascular endothelial growth factor 2 (VEGF2). The invention also relates to inhibiting the action of such polypeptide.

The formation of new blood vessels, or angiogenesis, is essential for embryonic development, subsequent growth, and tissue repair. Angiogenesis is an essential part of the growth of human solid cancer, and abnormal angiogenesis is associated with other diseases such as rheumatoid arthritis, psoriasis, and diabetic retinopathy (Folkman, J. and Klagsbrun, M., Science 235:442–447,(1987)).

Several factors are involved in angiogenesis. Both acidic and basic fibroblast growth factor molecules that are mitogens for endothelial cells and other cell types. Angiotropin and angiogenin can induce angiogenesis, although their functions are unclear (Folkman, J., 1993, Cancer Medicine pp. 153–170, Lea and Febiger Press). A highly selective mitogen for vascular endothelial cells is vascular endothelial growth factor or VEGF (Ferrara, N., et al., Endocr. Rev. 13:19–32, (1992)). Vascular endothelial growth factor is a secreted angiogenic mitogen whose target cell specificity appears to be restricted to vascular endothelial cells. The murine VEGF gene has been characterized and its expression pattern in embryogenesis has been analyzed. A persistent expression of VEGF was observed in epithelial cells adjacent to fenestrated endothelium, e.g., in choroid plexus and in kidney glomeruli. The data was consistent with a role of VEGF as a multifunctional regulator of endothelial cell growth and differentiation. Breier, G. et al. Development, 114:521–532 (1992).

VEGF can promote angiogenesis. VEGF shares sequence homology with human platelet-derived growth factor, PDGFα and PDGFβ ( Leung, D. W., et al., Science, 1306–1309, (1989)). The extent of homology is about 21% and 24% respectively. Eight cysteine residues are conserved between all three members. Although they are similar, there are specific differences between VEGF and PDGF. While PDGF is a major growth factor for connective tissue, VEGF is highly specific for endothelial cells. VEGF is also known as vascular permeability factor (VPM) and follicle stellate-derived growth factor. It is a heparin-binding dimeric polypeptide.

VEGF has four different forms of 121, 165, 189 and 206 amino acids due to alternative splicing. VEGF121 and VEGF165 are soluble and are capable of promoting angiogenesis, whereas VEGF189 and VEGF206 are bound to heparin containing proteoglycans in the cell surface. The temporal and spatial expression of VEGF has been correlated with physiological proliferation of the blood vessels (Gajdusek, C. M., and Carbon, S. J., Cell Physiol., 139:570–579, (1989)); McNeil, P. L., Muthukrishnan, L., Warder, E., D'Amore, P. A., J. Cell. Biol., 109:811–822, (1989)). Its high affinity binding sites are localized only on endothelial cells in tissue sections (Jakeman, L. B., et al., Clin. Invest. 89:244–253, (1989)). The factor can be isolated from pituitary cells and several tumor cell lines, and has been implicated in some human gliomas (Plate, K. H. Nature 359:845–848, (1992)).

Interestingly, expression of VEGF121 or VEGF165 confers on Chinese hamster ovary cells the ability to form tumors in nude mice (Ferrara, N., et al., J. Clin. Invest. 91:160–170, (1993)). Finally, the inhibition of VEGF function by anti-VEGF monoclonal antibodies was shown to inhibit tumor growth in immune-deficient mice (Kim, K. J., Nature 362:841–844, (1993)).

Vascular permeability factor, also known as VEGF, has also been found to be responsible for persistent microvascular hyperpermeability to plasma proteins even after the cessation of injury, which is a characteristic feature of normal wound healing. This suggests that VPF (or VEGF) is an important factor in wound healing. Brown, L. F. et al., J. Exp. Med., 176:1375–9 (1992).

U.S. Pat. No. 5,073,492, issued Dec. 17, 1991 to Chen et al., discloses a method for synergistically enhancing endothelial cell growth in an appropriate environment which comprises adding to the environment, VEGF, effectors and serum-derived factor. Also, vascular endothelial cell growth factor C sub-unit DNA has been prepared by polymerase chain reaction techniques. The DNA encodes a protein that may exist as either a heterodimer or homodimer. The protein is a mammalian vascular endothelial cell mitogen and, as such, is useful for the promotion of vascular development and repair, as disclosed in European Patent Application No. 92302750.2, published Sept. 30, 1992.

In accordance with one aspect of the present invention, there is provided a novel mature polypeptide which is a VEGF2 as well as fragments, analogs and derivatives thereof. The VEGF2 of the present invention is of human origin.

In accordance with another aspect of the present invention, there are provided polynucleotides (DNA or RNA) which encode such polypeptides. In accordance with still another aspect of the present invention, there is provided a process for producing such polypeptide by recombinant techniques.

In accordance with yet a further aspect of the present invention, there is provided a process for utilizing such polypeptide, or polynucleotide encoding such polypeptide, for therapeutic purposes, for example, as a wound-healing agent, to promote growth of damaged bone and tissue and promote endothelialization as well as for diagnosis of tumors, cancer therapy and to identify and isolate unknown receptors of VEGF2.

In accordance with yet another aspect of the present invention, there is provided an antibody against the VEGF2 and a process for producing such antibody.

In accordance with yet another aspect of the present invention, there are provided antagonist/inhibitors to VEGF2, which may be used to inhibit the action of such polypeptide, for example, to prevent tumor angiogenesis.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A, 1B, 1C and 1D (FIG. 1A shows the first portions of the polynucleotide sequence encoding VEGF2 and the amino acid sequence for VEGF2, and FIGS. 1B, 1C and 1D, respectively continue with the sequential portions of each sequence began in FIG. 1A) collectively depict the polynucleotide sequence (SEQ ID NO:1) which encodes VEGF2, and the corresponding amino acid sequence (SEQ ID NO:2) for the VEGF2 polypeptide comprising 350 amino acid residues of which approximately the first 24 amino acids represent the leader sequence. The standard one-letter codes are utilized to depict the amino acid residues encoded by the polynucleotide triplets. The polynucleotide sequence (SEQ ID NO:1) which encodes for VEGF2, and the corresponding deduced amino acid sequence (SEQ ID NO:2) of the full length VEGF2 polypeptide comprising 350 amino acid residues of which approximately the first 24 amino acids represent the leader sequence. The standard three-letter abbreviation has been used to depict the amino acid sequence.

FIGS. 2A and 2B collectively depict polypeptide sequences in alignment and show the alignment of VEGF2 with the other growth factor PDGFα, PDGFβ, and VEGF. FIG. 2A depicts N-terminal portions of the polypeptide sequences and FIG. 2A continues with C-terminal portions of the polypeptide sequences. The four lines in each comparative row depict, respectively, the PDGFα polypeptide sequence (SEQ ID NO:7), the PDGFβ polypeptide sequence (SEQ ID NO:8), the VEGF polypeptide sequence (SEQ ID NO:9) and the VEGF2 polypeptide sequence. The amino acid residues are illustrated in FIGS. 2A and 2B by the standard one-letter codes.

FIG. 3 shows, in table-form, the percent homology between PDGFα, PDGFβ, VEGF and VEGF2.

Figure 4:
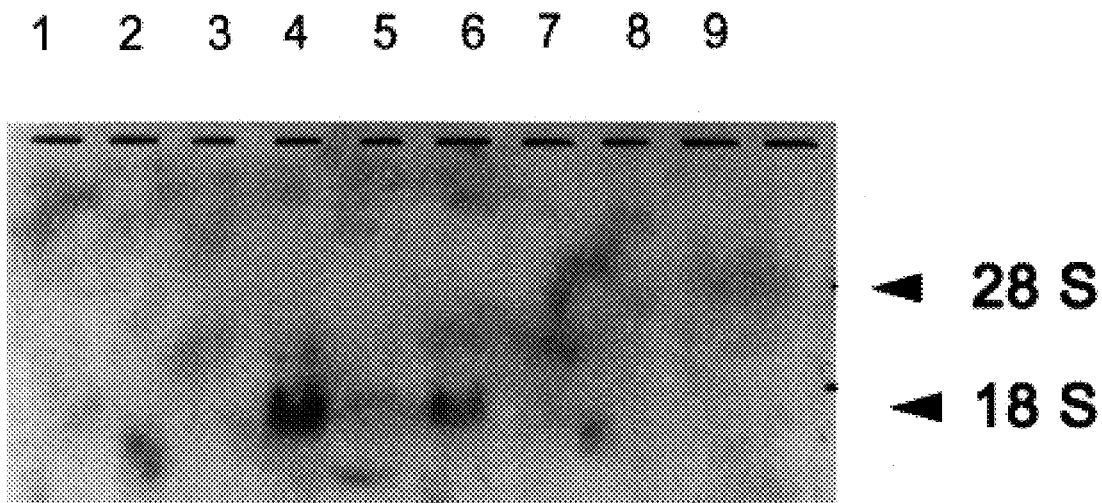
FIG. 4 shows the presence of mRNA for VEGF2 in breast tumor cell lines.

In accordance with one aspect of the present invention, there is provided an isolated nucleic acid (polynucleotide) which encodes for the mature polypeptide having the deduced amino acid sequence of SEQ ID NO:2 or for the mature polypeptide encoded by the cDNA of the clone deposited as ATCC Deposit No. 75698, on Mar. 4, 1994, with ATCC, 10801 University Boulevard, Manassas, Va. 20110-2209. Since the strain referred to is being maintained under the terms of the Budapest Treaty, it will be made available to a patent office signatory to the Budapest Treaty. If a patent should issue which is directed to the present invention, upon the issuance of such a patent the deposited strain of ATCC 75698 will be irrevocably and without restriction released to the public, excepting for those restrictions permitted by enforcement of the patent.

A polynucleotide encoding a polypeptide of the present invention may be obtained from early stage human embryo (week 8 to 9) osteoclastomas, adult heart or several breast cancer cell lines. The polynucleotide of this invention was discovered in a cDNA library derived from early stage human embryo week 9. It is structurally related to the VEGF/PDGF family. It contains an open reading frame encoding a protein of about 350 amino acid residues of which approximately the first 24 amino acid residues are likely to be leader sequence such that the mature protein comprises 326 amino acids, and which protein exhibits the highest homology to vascular endothelial growth factor (30% identity), followed by PDGFα (23%) and PDGFβ (22%), (see FIG. 3). It is particularly important that all eight cysteines are conserved within all four members of the family (see boxed areas of FIG. 2). In addition, the signature for the PDGF/VEGF family, PXCVXXXRCXGCCN, (SEQ ID NO:3) is conserved in VEGF2 (see FIG. 2). The homology between VEGF2, VEGF and the two PDGFs is at the protein sequence level. No nucleotide sequence homology can be detected, and therefore, it would be difficult to isolate the VEGF2 through simple approaches such as low stringency hybridization.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in SEQ ID NO:1 or that of the deposited clone or may be a different coding sequence which coding sequence, as a result of the redundancy or degeneracy of the genetic code, encodes the same, mature polypeptide as the DNA of SEQ ID NO:1 or the deposited cDNA.

The polynucleotide which encodes for the mature polypeptide of FIG. 1 or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 or the same mature polypeptide encoded by the cDNA of the deposited clone as well as variants of such polynucleotides which variants encode for an fragment, derivative or analog of the polypeptide of FIG. 1 or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in SEQ ID NO:1 or of the coding sequence of the deposited clone. As known in the art, an allelic variant is an alternate form of a polynucleotide sequence which have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of SEQ ID NO:2 or the deposited cDNA.

The deposit(s) referred to herein will be maintained under the Budapest Treaty on the International Recognition of the Deposit of Microorganisms for the purposes of Patent Procedure. These deposits are provided merely as a convenience and are not an admission that a deposit is required under 35 U.S.C. § 112. The sequence of the polynucleotides contained in the deposited materials, as well as the amino acid sequence of the polypeptides encoded thereby, are incorporated herein by reference and are controlling in the event of any conflict with the description of sequences herein. A license may be required to make, use or sell the deposited materials, and no such license is hereby granted.

The present invention further relates to a VEGF2 polypeptide which has the deduced amino acid sequence of SEQ ID NO:2 or which has the amino acid sequence encoded by the deposited cDNA, as well as fragments, analogs and derivatives of such polypeptide.

The terms "fragment," "derivative" and "analog" when referring to the polypeptide of SEQ ID NO:2 or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of SEQ ID NO:2 or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the VEGF2 genes. The culture conditions, such as temperature, pH and the like, are those previously used with the host cell selected for expression, and will be apparent to the ordinarily skilled artisan.

The polynucleotide of the present invention may be employed for producing a polypeptide by recombinant techniques. Thus, for example, the polynucleotide sequence may be included in any one of a variety of expression vehicles, in particular vectors or plasmids for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other plasmid or vector may be used as long as it is replicable and viable in the host.

As hereinabove described, the appropriate DNA sequence may be inserted into the vector by a variety of procedures. In general, the DNA sequence is inserted into an appropriate restriction endonuclease sites by procedures known in the art. Such procedures and others are deemed to be within the scope of those skilled in the art.

The DNA sequence in the expression vector is operatively linked to an appropriate expression control sequence(s)

(promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as herein above described, as well as an appropriate promoter or control sequence, may be employed to transform an appropriate host to permit the host to express the protein. As representative examples of appropriate hosts, there may be mentioned: bacterial cells, such as *E. Coli, Salmonella typhimurium Streptomyces;* fungal cells, such as yeast; insect cells, such as Drosophila and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE-9 (Qiagen), pBs, phagescript, PsiX174, pBluescript SK, pBsKS, pNH8a, pNH16a, pNH18a, pNH46a (Stratagene); pTrc99A, pKK223-3, pKK233-3, pDR540, PRIT5 (Pharmacia). Eukaryotic: pWLneo, pSV2cat, pOG44, pXT1, pSG (Stratagene) pSVK3, pBPV, PMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, 1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook. et al., Molecular Cloning: A Laboratory Manual, Second Edition, (Cold Spring Harbor, N.Y., 1989), the disclosure of which is hereby incorporated by reference.

Transcription of a DNA encoding the polypeptides of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

VEGF2 is recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. It is preferred to have low concentrations (approximately 0.1–5 mM) of calcium ion present during purification (Price, et al., J. Biol. Chem., 244:917 (1969)). Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated.

VEGF2 is useful as a wound healing agent, particularly where it is necessary to re-vascularize damaged tissues, or where new capillary angiogenesis is important. Therefore, it may be used for treatment of full-thickness wounds such as dermal ulcers, including pressure sores, venous ulcers, and diabetic ulcers. In addition, it can be used in the treatment of full-thickness burns and injuries where angiogenesis is desired to prepare the burn in injured sites for a skin graft and flap. In this case, it should be applied directly at the sites. Similar, VEGF2 can be used in plastic surgery when reconstruction is required following a burn, other trauma, or even for cosmetic purposes.

VEGF2 may also be used to induce the growth of damaged bone, periodontium or ligament tissue. It may be used in periodontal disease where VEGF2 is applied in a methylcellulose gel to the roots of the diseased teeth, the treatment could lead to the formation of new bone and cementum with collagen fiber ingrowths. It can be used for regenerating supporting tissues of teeth, including alveolar bone, cementum and periodontal ligament, that have been damaged by disease and trauma.

Since angiogenesis is important in keeping wounds clean and non-infected, VEGF2 may be used in association with surgery and following the repair of cuts. It should be particularly useful in the treatment of abdominal wounds where there is a high risk of infection.

VEGF2 can be used for the promotion of endothelialization in vascular graft surgery. In the case of vascular grafts using either transplanted or synthetic material, VEGF2 can be applied to the surface of the graft or at the junction to promote the growth of the vascular endothelial cells. One derivation of this is that VEGF2 can be used to repair the damage of myocardial infarction and other occasions where coronary bypass surgery is needed by stimulating the growth of the transplanted tissue. Related to this is the use of VEGF2 to repair the cardiac vascular system after ischemia.

The identification of VEGF2 can be used for the generation of certain inhibitors of vascular endothelial growth factor. Since angiogenesis and neovascularization are essential steps in solid tumor growth, inhibition of angiogenic activity of the vascular endothelial growth factor is very useful to prevent the further growth, retard, or even regress solid tumors. Although the level of expression of VEGF2 is extremely low in normal tissues including breast, it can be found expressed at moderate levels in at least two breast tumor cell lines that are derived from malignant tumors. It is, therefore, possible that VEGF2 is involved in tumor angiogenesis and growth.

VEGF2 can be used for in vitro culturing of vascular endothelial cells, where it can be added to the conditional medium to a concentration from 10 pg/ml to 10 ng/ml.

The polypeptide of the present invention may also be employed in accordance with the present invention by expression of such polypeptide in vivo, which is often referred to as "gene therapy."

Thus, for example, cells such as bone marrow cells may be engineered with a polynucleotide (DNA or RNA) encoding for the polypeptide ex vivo, the engineered cells are then provided to a patient to be treated with the polypeptide. Such methods are well-known in the art. For example, cells may be engineered by procedures known in the art by use of a retroviral particle containing RNA encoding for the polypeptide of the present invention.

Similarly, cells may be engineered in vivo for expression of the polypeptide in vivo, for example, by procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such methods should be apparent to those skilled in the art from the teachings of the present invention. For example, the expression vehicle for engineering cells may be other than a retroviral particle, for example, an adenovirus, which may be used to engineering cells in vivo after combination with a suitable delivery vehicle.

The polypeptide of the present invention may be employed in combination with a suitable pharmaceutical carrier. Such compositions comprise a therapeutically effective amount of the protein, and a pharmaceutically acceptable carrier or excipient.. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptide of the present invention may be employed on conjunction with other therapeutic compounds.

The pharmaceutical compositions may be administered in a convenient manner, such as the oral, and intravenous routes, and is preferably administered topically. The amounts and dosage regimens of VEGF2 administered to a subject will depend on a number of factors, such as the mode of administration, the nature of the condition being treated, the body weight of the subject being treated and the judgment of the prescribing physician. Generally speaking, it is given, for example, in therapeutically effective doses of at least about 10 µg/kg body weight and, in most cases, it would be administered in an amount not in excess of about 8 mg/kg body weight per day and preferably the dosage is from about 10 µg/kg body weight to about 1 mg/kg body weight daily, taking into the account the routes of administration, symptoms, etc.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphism's) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clone from which the EST was derived, and the longer the better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques. Pergamon Press, New York (1988).

Once a sequence has been mapped to a precise chromosomal location, the physical position of the sequence on the chromosome can be correlated with genetic map data. (Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The present invention is further directed to inhibiting VEGF2 in vivo by the use of antisense technology. Antisense technology can be used to control gene expression through triple-helix formation or antisense DNA or RNA, both of which methods are based on binding of a polynucleotide to DNA or RNA. For example, the 5' coding portion of the mature polynucleotide sequence, which encodes for the polypeptide of the present invention, is used to design an antisense RNA oligonucleotide of from 10 to 40 base pairs in length. A DNA oligonucleotide is designed to be complementary to a region of the gene involved in transcription (triple helix—see Lee et al, Nucl. Acids Res., 6:3073 (1979); Cooney et al, Science, 241:456 (1988); and Dervan et al, Science, 251: 1360 (1991), thereby preventing transcription and the production of VEGF2. The antisense RNA oligonucleotide hybridizes to the mRNA in vivo and blocks translation of an mRNA molecule into the VEGF2 (antisense—Okano, J. Neurochem., 56:560 (1991); Oligodeoxynucleotides as Antisense Inhibitors of Gene Expression, CRC Press, Boca Raton, Fla. (1988)).

Alternatively, the oligonucleotides described above can be delivered to cells by procedures in the art such that the anti-sense RNA or DNA may be expressed in vivo to inhibit production of VEGF2 in the manner described above.

Antisense constructs to VEGF2, therefore, may inhibit the angiogenic activity of the VEGF2 and prevent the further growth or even regress solid tumors, since angiogenesis and neovascularization are essential steps in solid tumor growth. These antisense constructs may also be used to treat rheumatoid arthritis, psoriasis and diabetic retinopathy which are all characterized by abnormal angiogenesis.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptide corresponding to a sequence of the present invention can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

Neutralization antibodies can be identified and applied to mask the vascular endothelial growth factor, and that has been shown in mice model systems against VEGF. VEGF2 can also be inactivated by certain dominant negative mutants within the gene itself. It is known that both PDGF$\alpha$ and $\beta$ form either heterodimers or homodimers, and VEGF forms homodimers. Similar interaction between VEGF2 could be expected. These antibodies therefore may be used to block the angiogenic activity of VEGF2 and retard the growth of solid tumors. These antibodies may also be used to treat inflammation caused by the increased vascular permeability which results from the presence of VEGF2.

These antibodies may further be used in an immunoassay to detect the presence of tumors in certain individuals. Enzyme immunoassay can be performed from the blood sample of an individual. Elevated levels of of VEGF2 can be considered diagnostic of cancer.

The present invention is also directed to antagonist/inhibitors of the polypeptides of the present invention. The antagonist/inhibitors are those which inhibit or eliminate the function of the polypeptide.

Thus, for example, antagonists bind to a polypeptide of the present invention and inhibit or eliminate its function. The antagonist, for example, could be an antibody against the polypeptide which binds to the polypeptide or, in some cases, an oligonucleotide. An example of an inhibitor is a small molecule which binds to and occupies the catalytic site of the polypeptide thereby making the catalytic site inaccessible to substrate such that normal biological activity is prevented. Examples of small molecules include but are not limited to small peptides or peptide-like molecules.

Truncated versions of VEGF2 can also be produced that are capable of interacting with wild type VEGF2 form dimers that fail activate endothelial cell growth, therefore inactivated the endogenous VEGF2. Or, mutant forms of VEGF2 form dimers themselves and occupies the ligand binding domain of the proper tyrosine Kinase receptors on the target cell surface, but fail to activate the cell growth.

Alternatively, antagonists to the polypeptides of the present invention may be employed which bind to the receptors to which a polypeptide of the present invention normally binds. The antagonists may be closely related proteins such that they recognize and bind to the receptor sites of the natural protein, however, they are inactive forms of the natural protein and thereby prevent the action of VEGF2 since receptor sites are occupied. In these ways, the action of the VEGF2 is prevented and the antagonist/inhibitors may be used therapeutically as an anti-tumor drug by occupying the receptor sites of tumors which are recognized by VEGF2 or by inactivating VEGF2 itself. The antagonist/inhibitors may also be used to prevent inflammation due to the increased vascular permeability action of VEGF2. The antagonist/inhibitors may also be used to treat solid tumor growth, diabetic retinopathy, psoriasis and rheumatoid arthritis.

The antagonist/inhibitors may be employed in a composition with a pharmaceutically acceptable carrier, e.g., as hereinabove described.

The present invention will be further described with reference to the following examples; however, it is to be understood that the present invention is not limited to such examples. All parts or amounts, unless otherwise specified, are by weight.

In order to facilitate understanding of the following examples, certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a poly-acrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described by the method of Graham, F. and Van der Eb, A., Virology, 52:456–457 (1973).

Figure 5:
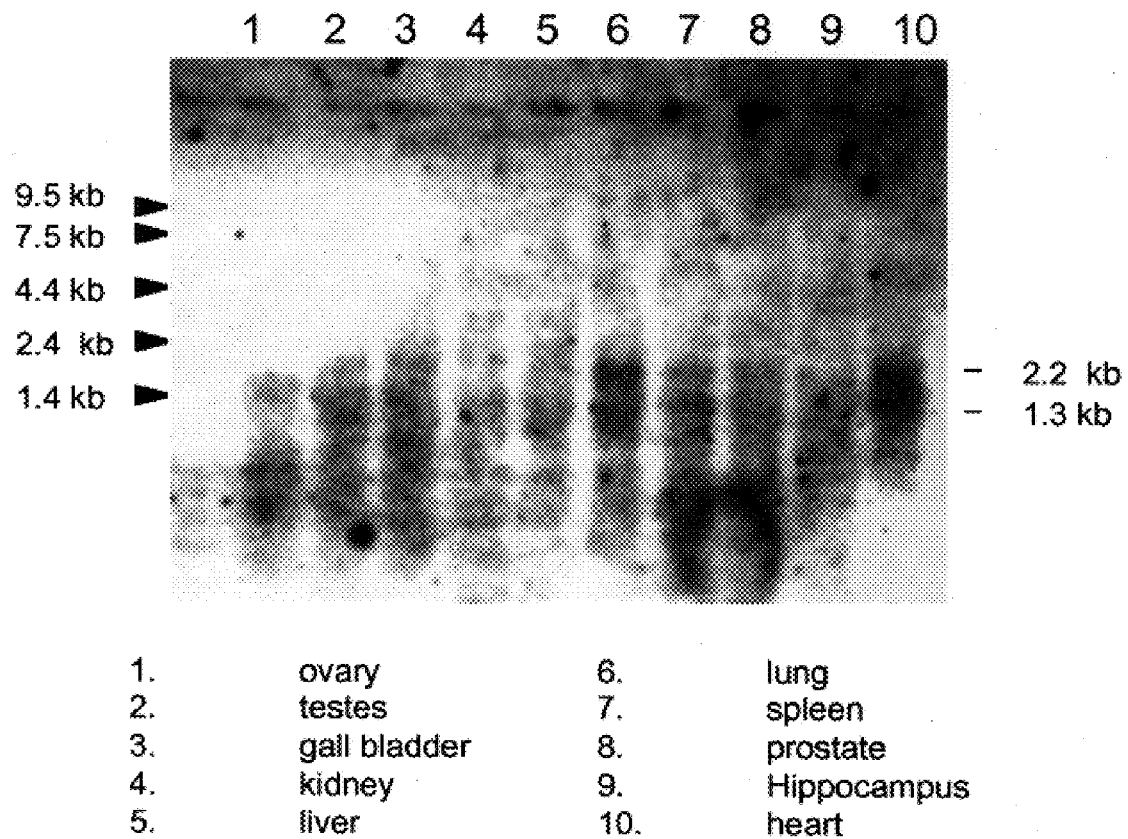
FIG. 5 depicts the results of a Northern blot analysis of VEGF2 in human adult tissues.

EXAMPLE 1
Expression, pattern of VEGF2 in human tissues and breast cancer cell lines Northern blot analysis was carried out to examine the levels of expression of VEGF2 in human tissues and breast cancer cell lines in human tissues. Total cellular RNA samples were isolated with RNAzol™ B system (Biotecx Laboratories, Inc.). About 10 μg of total RNA isolated from each breast tissue and cell line specified was separated on 1% agarose gel and blotted onto a nylon filter, (Molecular Cloning, Sambrook Fritsch, and Maniatis, Cold Spring Harbor Press, 1989). The labeling reaction was done according to the Stratagene Prime-It kit with 50 ng DNA fragment. The labeled DNA was purified with a Select-G-50 column from 5' Prime—3 Prime, Inc. The filter was then hybridized with radioactive labeled full length VEGF2 gene at 1,000,000 cpm/ml in 0.5 M NaPO$_4$ and 7% SDS overnight at 65° C. After wash twice at room temperature and twice at 60° C. with 0.5 X SSC, 0.1% SDS, the filters were then exposed at −70° C. overnight with intensifying screen. A message of 1.6 Kb was observed in 2 breast cancer cell lines. Lane #4 represents a very tumorigenic cell line that is estrogen independent for growth. See FIG. 4. Also, 10 μg of totall RNA from 10 human adult tissues were separated on an agarose gel and blotted onto a nylon filter. The filter was then hybridized with radioactively labeled VEGF2 probe in 7% SDS, 0.5 M NaPO$_4$, pH 7.2; 1% BSA overnight at 65° C. Following was in 0.2 X SSC at 65° C., the filter was exposed to film for 24 days at −70° C. with intensifying screen. See FIG. 5.

EXAMPLE 2
Expression of VEGF2 by in vitro transcripti I on and translation

The VEGF2 cDNA was transcribed and translated in vitro to determine the size of the translatable polypeptide encoded by the full length and partial VEGF2 cDNA. The full length and partial cDNA inserts of VEGF2 in the pBluescript SK vector were amplified by PCR with three paris of primers, 1) M13-reverse and forward primers; 2) M13-reverse primer and VEGF primer F4; 3) M13-reverse primer and VEGF primer F5. The sequence of these primers are as follows.

M13-2 reverse primer:
5'-ATGCTTCCGGCTCGTATG-3' (SEQ ID NO:4)

This sequence is located upstream of the 5' end of the VEGF2 cDNA insert in the pBluescript vector and is in an anti-sense orientation as the cDNA. A T3 promoter sequence is located between this primer and the VEGF2 cDNA.

M13-2 forward primer:
5'GGGTTTTCCCAGTCACGAC-3' (SEQ ID NO:5)

This sequence is located downstream of the 3' end of the VEGF2 cDNA insert in the pBluescript vector and is in an anti-sense orientation as the cDNA insert.

VEGF primer F4:
5'-CCACATGGTTCAGGAAAGACA-3' (SEQ ID NO:6)

This sequence is located within the VEGF2 cDNA in an anti-sense orientation from bp 1259–1239, which is about 169 bp away from the 3' end of the stop codon and about 266 bp before the last nucleotide of the cDNA.

PCR reaction with all three pairs of primers produce amplified products with T3 promoter sequence in front of the cDNA insert. THe first and third pairs of primers produce PCR products that encode the full polypeptide of VEGF2. The second pair of primers produce PCR product that misses 36 amino acids coding sequence at the C-terminus of the VEGF2 polypeptide.

Approximately 0.5 ug of PCR product from first pair of primers, 1 ug from second pair of primers, 1 ug from third pair of primers were used for in vitro transcription/translation. The in vitro transcription/translation reaction was performed in a 25 ul of volume, using the T$_N$T™ Coupled Reticulocyte Lysate Systems (promega, CAT# L4950). Specifically, the reaction contains 12.5 ul of TNT rabbit reticulocyte lysate 2 ul of TNT reaction buffer, 1 ul of T3 polymerase, 1 ul of 1 mM amino acide mixtrue (minus methionine), 4 ul of $^{35}$S -methionine (>1000 Ci/mmol, 10 mCi/ml), 1 ul of 40 U/ul; RNasin ribonuclease inhibitor, 0.5 or 1 ug of PCR products. Nuclease-free H$_2$O were added to bring the me to 25 ul. The reaction was incubated at 30° C. for 2 hours. Five microliters of the reaction product was analyzed on a 4–20% gradient SDS-PAGE gel. After fixing in 25% isopropanol and 10% acetic acid, the gel was dried and exposed to an X-ray film overnight at 70° C.

Figure 6:
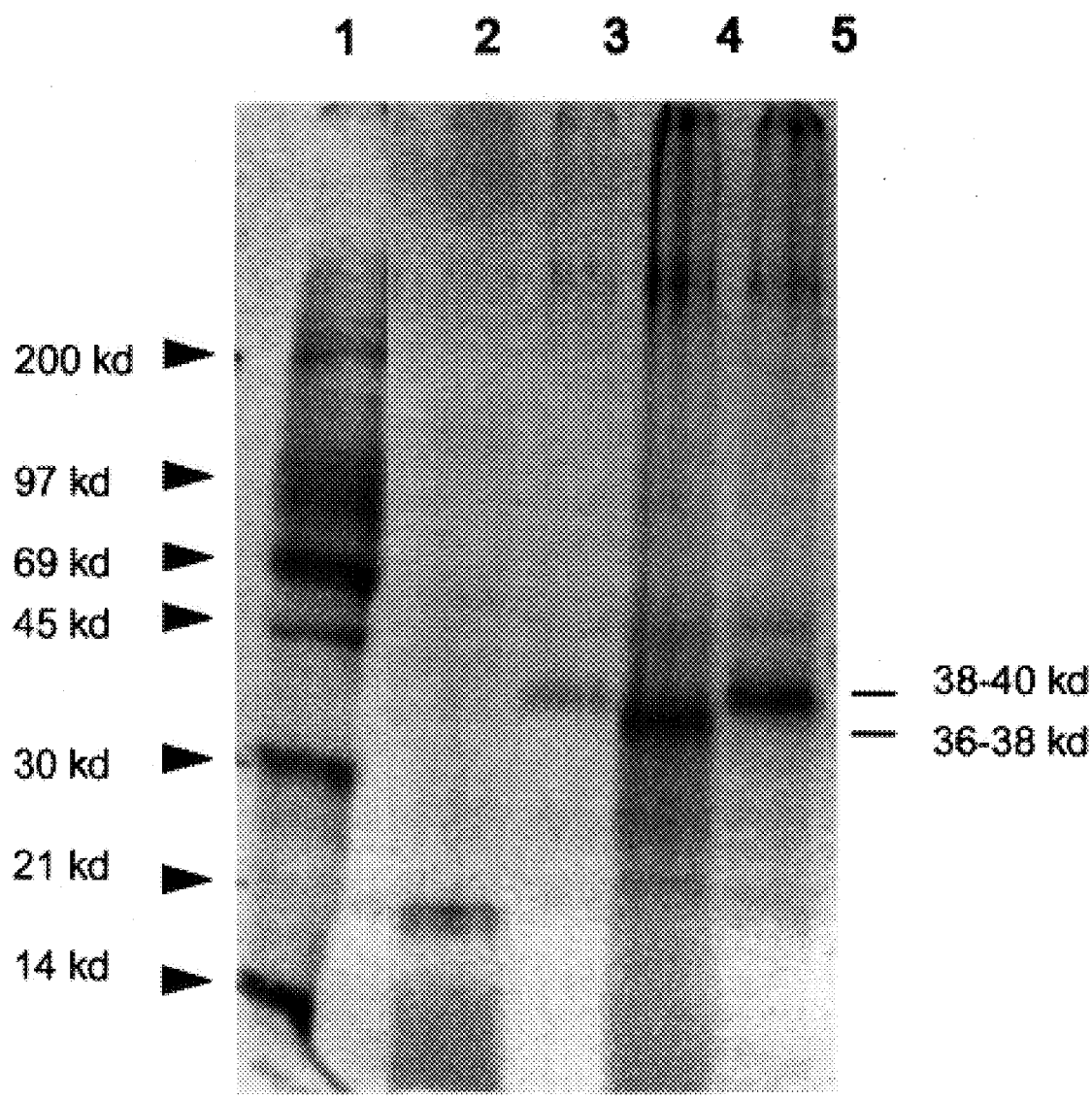
FIG. 6 shows the results of running VEGF2 and SDS-PAGE gel after in vitro transcription/translation. The full length and partial VEGF2 cDNA were transcribed and translated in a coupled reaction in the presence of $^{35}$S-methionine. The translated products were analyzed by 4–20% gradient SDS PAGE and exposed to X-ray film.

As shown in FIG. 6, PCR products containing the full length VEGF2 cDNA and the cDNA missing 266 bp in the 3' untranslated region (3'-UTR) produced the same length of translated products, whose molecular weights are estimated to be 38–40 dk (lanes 1 & 3). The cDNA missing all the 3'UTR and missing sequence encoding the C-terminal 36 amino acids was translated into a polypeptide with an estimated molecular weight of 36–38 kd (lane 2).

What is claimed is:

1. An isolated polynucleotide encoding a mature portion of a protein consisting of SEQ ID NO:2.

2. The isolated polynucleotide of claim 1 encoding a proprotein portion of a protein consisting of SEQ ID NO:2.

3. The polynucleotide of claim 2 fused to a polynucleotide which encodes a heterologous polypeptide.

4. A recombinant vector comprising the polynucleotide of claim 2.

5. A recombinant vector comprising the polynucleotide of claim 2 operatively associated with a regulatory sequence that controls gene expression.

6. A genetically engineered host cell comprising the polynucleotide of claim 2.

7. A genetically engineered host cell comprising the polynucleotide of claim 2 operatively associated with a heterologous regulatory sequence that controls gene expression.

8. A method for producing a VEGF-2 polypeptide, comprising:
  (a) culturing the genetically engineered host cell of claim 7 under conditions suitable to produce the polypeptide; and
  (b) recovering the polypeptide from the cell culture.

9. The polynucleotide of claim 2 fused to a heterologous polynucleotide.

10. The polynucleotide of claim 1 fused to a polynucleotide which encodes a heterologous polypeptide.

11. A recombinant vector comprising the polynucleotide of claim 1.

12. A recombinant vector comprising the polynucleotide of claim 1 operatively associated with a regulatory sequence that controls gene expression.

13. A genetically engineered host cell comprising the polynucleotide of claim 1.

14. A genetically engineered host cell comprising the polynucleotide of claim 1 operatively associated with a heterologous regulatory sequence that controls gene expression.

15. A method for producing a VEGF-2 polypeptide, comprising:
  (a) culturing the genetically engineered host cell of claim 14 under conditions suitable to produce the polypeptide; and
  (b) recovering the polypeptide from the cell culture.

16. The polynucleotide of claim 1 fused to a heterologous polynucleotide.

17. An isolated polynucleotide which encodes a polypeptide comprising amino acids 61–74 of SEQ ID NO:2.

18. The isolated polynucleotide of claim 17, wherein the polypeptide comprises amino acids 1–326 of SEQ ID NO:2.

19. The polynucleotide of claim 18 fused to a polynucleotide which encodes a heterologous polypeptide.

20. A recombinant vector comprising the polynucleotide of claim 18.

21. A recombinant vector comprising the polynucleotide of claim 18 operatively associated with a regulatory sequence that controls gene expression.

22. A genetically engineered host cell comprising the polynucleotide of claim 18.

23. A genetically engineered host cell comprising the polynucleotide of claim 18 operatively associated with a heterologous regulatory sequence that controls gene expression.

24. A method for producing a VEGF-2 polypeptide, comprising:
  (a) culturing the genetically engineered host cell of claim 23 under conditions suitable to produce the polypeptide; and
  (b) recovering the polypeptide from the cell culture.

25. The polynucleotide of claim 18 fused to a heterologous polynucleotide.

26. The isolated polynucleotide of claim 17, wherein the polypeptide comprises amino acids −24–326 of SEQ ID NO:2.

27. The polynucleotide of claim 26 fused to a polynucleotide which encodes a heterologous polypeptide.

28. A recombinant vector comprising the polynucleotide of claim 26.

29. A recombinant vector comprising the polynucleotide of claim 26 operatively associated with a regulatory sequence that controls gene expression.

30. A genetically engineered host cell comprising the polynucleotide of claim 26.

31. A genetically engineered host cell comprising the polynucleotide of claim 26 operatively associated with a heterologous regulatory sequence that controls gene expression.

32. A method for producing a VEGF-2 polypeptide, comprising:
  (a) culturing the genetically engineered host cell of claim 31 under conditions suitable to produce the polypeptide; and
  (b) recovering the polypeptide from the cell culture.

33. The polynucleotide of claim 26 fused to a heterologous polynucleotide.

34. The polynucleotide of claim 17 fused to a polynucleotide which encodes a heterologous polypeptide.

35. A recombinant vector comprising the polynucleotide of claim 17.

36. A recombinant vector comprising the polynucleotide of claim 17 operatively associated with a regulatory sequence that controls gene expression.

37. A genetically engineered host cell comprising the polynucleotide of claim 17.

38. A genetically engineered host cell comprising the polynucleotide of claim 17 operatively associated with a heterologous regulatory sequence that controls gene expression.

39. A method for producing a VEGF-2 polypeptide, comprising:
  (a) culturing the genetically engineered host cell of claim 38 under conditions suitable to produce the polypeptide; and
  (b) recovering the polypeptide from the cell culture.

40. The polynucleotide of claim 17 fused to a heterologous polynucleotide.

41. An isolated polynucleotide which hybridizes to a polynucleotide consisting of a nucleotide sequence of SEQ ID NO: 1 or the complement of SEQ ID NO: 1 under the following conditions: hybridization in 0.5M $NaPO_4$, 7% sodium dodecyl sulfate (SDS) at 65° C. and washing with 0.5×SSC. 0.1% SDS at 60° C.

42. The isolated polynucleotide of claim 41, wherein the polynucleotide is DNA.

43. The isolated polynucleotide of claim 41, wherein the polynucleotide is RNA.

44. The polynucleotide of claim 41 fused to a polynucleotide which encodes a heterologous polypeptide.

45. A recombinant vector comprising the polynucleotide of claim 41.

46. A recombinant vector comprising the polynucleotide of claim 41 operatively associated with a regulatory sequence that controls gene expression.

47. A genetically engineered host cell comprising the polynucleotide of claim 41.

48. A genetically engineered host cell comprising the polynucleotide of claim 41 operatively associated with a heterologous regulatory sequence that controls gene expression.

49. The polynucleotide of claim 41 fused to a heterologous polynucleotide.

50. An isolated polynucleotide which hybridizes to the cDNA contained in ATCC Deposit No. 75968 under the following conditions: hybridization in 0.5M $NaPO_1$, 7% sodium dodecyl sulfate (SDS) at 65° C. and washing with 0.5×SSC, 0.1% SDS at 60° C.

51. The isolated polynucleotide of claim 50, wherein the polynucleotide is DNA.

52. The isolated polynucleotide of claim 50, wherein the polynucleotide is RNA.

53. The polynucleotide of claim 50 fused to a polynucleotide which encodes a heterologous polypeptide.

54. A recombinant vector comprising the polynucleotide of claim 50.

55. A recombinant vector comprising the polynucleotide of claim 50 operatively associated with a regulatory sequence that controls gene expression.

56. A genetically engineered host cell comprising the polynucleotide of claim 50.

57. A genetically engineered host cell comprising the polynucleotide of claim 50 operatively associated with a heterologous regulatory sequence that controls gene expression.

58. A method for producing a VEGF-2 polypeptide, comprising:
(a) culturing the genetically engineered host cell of claim 57 under conditions suitable to produce the polypeptide; and
(b) recovering the polypeptide from the cell culture.

59. The polynucleotide of claim 50 fused to a heterologous polynucleotide.

60. A method for producing a VEGF-2 polypeptide, comprising:
(a) culturing a genetically engineered host cell comprising an isolated mammalian RNA or cDNA which hybridizes to a polynucleotide consisting of a nucleic sequence or the complement of SEQ ID NO:1 under the following conditions; hybridization in 0.5M NaPO$_4$ 7% sodium dodecyl sulfate (SDS) at 65° C. and washing with 0.5×SSC 0.1% SDS at 60° C. under conditions suitable to produce the polypeptide; and
(b) recovering the polypeptide from the cell culture.

61. An isolated polynucleotide comprising a polynucleotide that encodes a polypeptide fragment of SEQ ID NO:2, wherein said polypeptide fragment has angiogenic activity.

62. The polynucleotide of claim 61 fused to a heterologous polynucleotide.

63. The polynucleotide of claim 61 fused to a polynucleotide which encodes a heterologous polypeptide.

64. A recombinant vector comprising the polynucleotide of claim 61.

65. A recombinant vector comprising the polynucleotide of claim 61 operatively associated with a regulatory sequence that controls gene expression.

66. A genetically engineered host cell comprising the polynucleotide of claim 61.

67. A genetically engineered host cell comprising the polynucleotide of claim 61 operatively associated with a heterologous regulatory sequence that controls gene expression.

68. A method for producing a VEGF-2 polypeptide, comprising:
(a) culturing the genetically engineered host cell of claim 67 under conditions suitable to produce the polypeptide; and
(b) recovering the polypeptide from the cell culture.

69. An isolated polynucleotide comprising a polynucleotide that encodes a polypeptide fragment encoded by the cDNA contained in ATCC Deposit No. 75968, wherein said fragment has angiogenic activity.

70. The polynucleotide of claim 69 fused to a heterologous polynucleotide.

71. The polynucleotide of claim 69 fused to a polynucleotide which encodes a heterologous polypeptide.

72. A recombinant vector comprising the polynucleotide of claim 69.

73. A recombinant vector comprising the polynucleotide of claim 69 operatively associated with a regulatory sequence that controls gene expression.

74. A genetically engineered host cell comprising the polynucleotide of claim 69.

75. A genetically engineered host cell comprising the polynucleotide of claim 69 operatively associated with a heterologous regulatory sequence that controls gene expression.

76. A method for producing a VEGF-2 polypeptide, comprising:
(a) culturing the genetically engineered host cell of claim 75 under conditions suitable to produce the polypeptide; and
(b) recovering the polypeptide from the cell culture.

77. An isolated polynucleotide comprising a polynucleotide that encodes a polypeptide fragment of SEQ ID NO:2, wherein said polypeptide fragment has endothelial cell proliferative activity.

78. The polynucleotide of claim 77 fused to a heterologous polynucleotide.

79. The polynucleotide of claim 77 fused to a polynucleotide which encodes a heterologous polypeptide.

80. A recombinant vector comprising the polynucleotide of claim 77.

81. A recombinant vector comprising the polynucleotide of claim 77 operatively associated with a regulatory sequence that controls gene expression.

82. A genetically engineered host cell comprising the polynucleotide of claim 77.

83. A genetically engineered host cell comprising the polynucleotide of claim 77 operatively associated with a heterologous regulatory sequence that controls gene expression.

84. A method for producing a VEGF-2 polypeptide, comprising:
(a) culturing the genetically engineered host cell of claim 83 under conditions suitable to produce the polypeptide; and
(b) recovering the polypeptide from the cell culture.

85. An isolated polynucleotide comprising a polynucleotide that encodes a polypeptide fragment encoded by the cDNA contained in ATCC Deposit No. 75968, wherein said fragment has endothelial cell proliferative activity.

86. The polynucleotide of claim 85 fused to a heterologous polynucleotide.

87. The polynucleotide of claim 85 fused to a polynucleotide which encodes a heterologous polypeptide.

88. A recombinant vector comprising the polynucleotide of claim 85.

89. A recombinant vector comprising the polynucleotide of claim 85 operatively associated with a regulatory sequence that controls gene expression.

90. A genetically engineered host cell comprising the polynucleotide of claim 85.

91. A genetically engineered host cell comprising the polynucleotide of claim 85 operatively associated with a heterologous regulatory sequence that controls gene expression.

92. A method for producing a VEGF-2 polypeptide, comprising:

(a) culturing the genetically engineered host cell of claim 91 under conditions suitable to produce the polypeptide; and (b) recovering the polypeptide from the cell culture.

93. An isolated polynucleotide encoding a mature portion of a protein encoded by the cDNA contained in ATCC Deposit No. 75968.

94. The polynucleotide of claim 93 fused to a heterologous polynucleotide.

95. The polynucleotide of claim 93 fused to a polynucleotide which encodes a heterologous polypeptide.

96. A recombinant vector comprising the polynucleotide of claim 93.

97. A recombinant vector comprising the polynucleotide of claim 93 operatively associated with a regulatory sequence that controls gene expression.

98. A genetically engineered host cell comprising the polynucleotide of claim 93.

99. A genetically engineered host cell comprising the polynucleotide of claim 93 operatively associated with a heterologous regulatory sequence that controls gene expression.

100. A method for producing a VEGF-2 polypeptide, comprising:

(a) culturing the genetically engineered host cell of claim 99 under conditions suitable to produce the polypeptide; and (b) recovering the polypeptide from the cell culture.

101. An isolated polynucleotide encoding a proprotein portion of a protein encoded by the cDNA contained in ATCC Deposit No. 75968.

102. The polynucleotide of claim 101 fused to a heterologous polynucleotide.

103. The polynucleotide of claim 101 fused to a polynucleotide which encodes a heterologous polypeptide.

104. A recombinant vector comprising the polynucleotide of claim 101.

105. A recombinant vector comprising the polynucleotide of claim 101 operatively associated with a regulatory sequence that controls gene expression.

106. A genetically engineered host cell comprising the polynucleotide of claim 101.

107. A genetically engineered host cell comprising the polynucleotide of claim 101 operatively associated with a heterologous regulatory sequence that controls gene expression.

108. A method for producing a VEGF-2 polypeptide, comprising:

(a) culturing the genetically engineered host cell of claim 107 under conditions suitable to produce the polypeptide; and (b) recovering the polypeptide from the cell culture.

109. An isolated polynucleotide encoding a protein encoded by the cDNA contained in ATCC Deposit No. 75968.

110. The polynucleotide of claim 109 fused to a heterologous polynucleotide.

111. The polynucleotide of claim 109 fused to a polynucleotide which encodes a heterologous polypeptide.

112. A recombinant vector comprising the polynucleotide of claim 109.

113. A recombinant vector comprising the polynucleotide of claim 109 operatively associated with a regulatory sequence that controls gene expression.

114. A genetically engineered host cell-comprising the polynucleotide of claim 109.

115. A genetically engineered host cell comprising the polynucleotide of claim 109 operatively associated with a heterologous regulatory sequence that controls gene expression.

116. A method for producing a VEGF-2 polypeptide, comprising:

(a) culturing the genetically engineered host cell of claim 115 under conditions suitable to produce the polypeptide; and (b) recovering the polypeptide from the cell culture.

* * * * *

UNITED STATES PATENT AND TRADEMARK OFFICE
CERTIFICATE OF CORRECTION

PATENT NO. : 5,935,820
DATED : August 10, 1999
INVENTOR(S) : HU, et. al.

It is certified that error appears in the above-identified patent and that said Letters Patent is hereby corrected as shown below:

Column 5, line 29, change "polynucleotides . As" to -- polynucleotides. As--.

Claim 41, line 39, replace "NaPO,." with --NaPO$_4$--;

line 40, replace "C." with --C,--; and line 41, replace "0.5xSSC." with --0.5xSSC.--.

Claim 50, line 62, replace "75968" with --75698--;

line 63, replace "NaPO$_1$," with --NaPO$_4$--; and line 64, replace "C." with --C,--.

Claim 60, line 31, replace "conditions;" with --conditions:--; and line 33, after "0.5xSSC" insert --,-- and replace "C." with --C--.

Claim 69, line 62, replace "75968" with --75698--.

Claim 85, line 50, replace "75968" with --75698--.

Claim 93, line 9, replace "75968" with --75698--.

Claim 101, line 34, replace "75968" with --75698--.

Claim 109, line 17, replace "75968" with --75698--.

Signed and Sealed this

Twenty-sixth Day of December, 2000

*Attest:*

Q. TODD DICKINSON

*Attesting Officer*     *Director of Patents and Trademarks*

SEQUENCE LISTING

```
<160> NUMBER OF SEQ ID NOS: 9

<210> SEQ ID NO 1
<211> LENGTH: 1525
<212> TYPE: DNA
<213> ORGANISM: Homo sapiens
<220> FEATURE:
<221> NAME/KEY: CDS
<222> LOCATION: (71)..(1120)
<220> FEATURE:
<221> NAME/KEY: sig_peptide
<222> LOCATION: (71)..(142)
<220> FEATURE:
<221> NAME/KEY: mat_peptide
<222> LOCATION: (143)..(1120)
```

<400> SEQUENCE: 1

```
cgaggccacg gcttatgcaa gcaaagatct ggaggagcag ttacggtctg tgtccagtgt      60
agatgaactc atg act gta ctc tac cca gaa tat tgg aaa atg tac aag        109
           Met Thr Val Leu Tyr Pro Glu Tyr Trp Lys Met Tyr Lys
               -20                     -15 tgt cag cta agg aaa gga ggc tgg caa cat aac aga gaa cag gcc aac        157
Cys Gln Leu Arg Lys Gly Gly Trp Gln His Asn Arg Glu Gln Ala Asn
    -10                  -5                  -1  1                 5 ctc aac tca agg aca gaa gag act ata aaa ttt gct gca gca cat tat        205
Leu Asn Ser Arg Thr Glu Glu Thr Ile Lys Phe Ala Ala Ala His Tyr
                 10                  15                  20 aat aca gag atc ttg aaa agt att gat aat gag tgg aga aag act caa        253
Asn Thr Glu Ile Leu Lys Ser Ile Asp Asn Glu Trp Arg Lys Thr Gln
             25                  30                  35 tgc atg cca cgg gag gtg tgt ata gat gtg ggg aag gag ttt gga gtc        301
Cys Met Pro Arg Glu Val Cys Ile Asp Val Gly Lys Glu Phe Gly Val
         40                  45                  50 gcg aca aac acc ttc ttt aaa cct cca tgt gtg tcc gtc tac aga tgt        349
Ala Thr Asn Thr Phe Phe Lys Pro Pro Cys Val Ser Val Tyr Arg Cys
     55                  60                  65 ggg ggt tgc tgc aat agt gag ggg ctg cag tgc atg aac acc agc acg        397
Gly Gly Cys Cys Asn Ser Glu Gly Leu Gln Cys Met Asn Thr Ser Thr
 70                  75                  80                  85 agc tac ctc agc aag acg tta ttt gaa att aca gtg cct ctc tct caa        445
Ser Tyr Leu Ser Lys Thr Leu Phe Glu Ile Thr Val Pro Leu Ser Gln
                 90                  95                 100 ggc ccc aaa cca gta aca atc agt ttt gcc aat cac act tcc tgc cga        493
Gly Pro Lys Pro Val Thr Ile Ser Phe Ala Asn His Thr Ser Cys Arg
             105                 110                 115 tgc atg tct aaa ctg gat gtt tac aga caa gtt cat tcc att att aga        541
Cys Met Ser Lys Leu Asp Val Tyr Arg Gln Val His Ser Ile Ile Arg
         120                 125                 130 cgt tcc ctg cca gca aca cta cca cag tgt cag gca gcg aac aag acc        589
Arg Ser Leu Pro Ala Thr Leu Pro Gln Cys Gln Ala Ala Asn Lys Thr
     135                 140                 145 tgc ccc acc aat tac atg tgg aat aat cac atc tgc aga tgc ctg gct        637
Cys Pro Thr Asn Tyr Met Trp Asn Asn His Ile Cys Arg Cys Leu Ala
150                 155                 160                 165 cag gaa gat ttt atg ttt tcc tcg gat gct gga gat gac tca aca gat        685
Gln Glu Asp Phe Met Phe Ser Ser Asp Ala Gly Asp Asp Ser Thr Asp
                 170                 175                 180 gga ttc cat gac atc tgt gga cca aac aag gag ctg gat gaa gag acc        733
Gly Phe His Asp Ile Cys Gly Pro Asn Lys Glu Leu Asp Glu Glu Thr
             185                 190                 195 tgt cag tgt gtc tgc aga gcg ggg ctt cgg cct gcc agc tgt gga ccc        781
Cys Gln Cys Val Cys Arg Ala Gly Leu Arg Pro Ala Ser Cys Gly Pro
         200                 205                 210 cac aaa gaa cta gac aga aac tca tgc cag tgt gtc tgt aaa aac aaa        829
His Lys Glu Leu Asp Arg Asn Ser Cys Gln Cys Val Cys Lys Asn Lys
     215                 220                 225 ctc ttc ccc agc caa tgt ggg gcc aac cga gaa ttt gat gaa aac aca        877
Leu Phe Pro Ser Gln Cys Gly Ala Asn Arg Glu Phe Asp Glu Asn Thr
230                 235                 240                 245 tgc cag tgt gta tgt aaa aga acc tgc ccc aga aat caa ccc cta aat        925
Cys Gln Cys Val Cys Lys Arg Thr Cys Pro Arg Asn Gln Pro Leu Asn
                 250                 255                 260 cct gga aaa tgt gcc tgt gaa tgt aca gaa agt cca cag aaa tgc ttg        973
Pro Gly Lys Cys Ala Cys Glu Cys Thr Glu Ser Pro Gln Lys Cys Leu
             265                 270                 275
```

```
                                                                               -continued tta aaa gga aag aag ttc cac cac caa aca tgc agc tgt tac aga cgg               1021
Leu Lys Gly Lys Lys Phe His His Gln Thr Cys Ser Cys Tyr Arg Arg
        280                 285                 290 cca tgt acg aac cgc cag aag gct tgt gag cca gga ttt tca tat agt               1069
Pro Cys Thr Asn Arg Gln Lys Ala Cys Glu Pro Gly Phe Ser Tyr Ser
    295                 300                 305 gaa gaa gtg tgt cgt tgt gtc cct tca tat tgg caa aga cca caa atg               1117
Glu Glu Val Cys Arg Cys Val Pro Ser Tyr Trp Gln Arg Pro Gln Met
310                 315                 320                 325 agc taagattgta ctgttttcca gttcatcgat tttctattat ggaaaactgt                    1170
Ser gttgccacag tagaactgtc tgtgaacaga gagacccttg tgggtccatg ctaacaaga              1230 caaaagtctg tctttcctga accatgtgga taactttaca gaaatggact ggagctcatc            1290
tgcaaaaggc ctcttgtaaa gactggtttt ctgccaatga ccaaacagcc aagattttcc            1350
tcttgtgatt tctttaaaag aatgactata taatttattt ccactaaaaa tattgtttct            1410
gcattcattt ttatagcaac aacaattggt aaaactcact gtgatcaata tttttatatc            1470
atgcaaaata tgtttaaaat aaaatgaaaa ttgtattata aaaaaaaaaa aaaaa                 1525

<210> SEQ ID NO 2
<211> LENGTH: 350
<212> TYPE: PRT
<213> ORGANISM: Homo sapiens

<400> SEQUENCE: 2

Met Thr Val Leu Tyr Pro Glu Tyr Trp Lys Met Tyr Lys Cys Gln Leu
                -20                 -15                 -10

Arg Lys Gly Gly Trp Gln His Asn Arg Glu Gln Ala Asn Leu Asn Ser
            -5                  -1   1               5

Arg Thr Glu Glu Thr Ile Lys Phe Ala Ala Ala His Tyr Asn Thr Glu
    10                  15                  20

Ile Leu Lys Ser Ile Asp Asn Glu Trp Arg Lys Thr Gln Cys Met Pro
25                  30                  35                  40

Arg Glu Val Cys Ile Asp Val Gly Lys Glu Phe Gly Val Ala Thr Asn
                45                  50                  55

Thr Phe Phe Lys Pro Pro Cys Val Ser Val Tyr Arg Cys Gly Gly Cys
            60                  65                  70

Cys Asn Ser Glu Gly Leu Gln Cys Met Asn Thr Ser Thr Ser Tyr Leu
        75                  80                  85

Ser Lys Thr Leu Phe Glu Ile Thr Val Pro Leu Ser Gln Gly Pro Lys
    90                  95                  100

Pro Val Thr Ile Ser Phe Ala Asn His Thr Ser Cys Arg Cys Met Ser
105                 110                 115                 120

Lys Leu Asp Val Tyr Arg Gln Val His Ser Ile Ile Arg Arg Ser Leu
                125                 130                 135

Pro Ala Thr Leu Pro Gln Cys Gln Ala Ala Asn Lys Thr Cys Pro Thr
            140                 145                 150

Asn Tyr Met Trp Asn Asn His Ile Cys Arg Cys Leu Ala Gln Glu Asp
        155                 160                 165

Phe Met Phe Ser Ser Asp Ala Gly Asp Asp Ser Thr Asp Gly Phe His
    170                 175                 180

Asp Ile Cys Gly Pro Asn Lys Glu Leu Asp Glu Glu Thr Cys Gln Cys
185                 190                 195                 200

Val Cys Arg Ala Gly Leu Arg Pro Ala Ser Cys Gly Pro His Lys Glu
                205                 210                 215
```

```
Leu Asp Arg Asn Ser Cys Gln Cys Val Cys Lys Asn Lys Leu Phe Pro
                220                 225                 230

Ser Gln Cys Gly Ala Asn Arg Glu Phe Asp Glu Asn Thr Cys Gln Cys
            235                 240                 245

Val Cys Lys Arg Thr Cys Pro Arg Asn Gln Pro Leu Asn Pro Gly Lys
    250                 255                 260

Cys Ala Cys Glu Cys Thr Glu Ser Pro Gln Lys Cys Leu Leu Lys Gly
265                 270                 275                 280

Lys Lys Phe His His Gln Thr Cys Ser Cys Tyr Arg Arg Pro Cys Thr
                285                 290                 295

Asn Arg Gln Lys Ala Cys Glu Pro Gly Phe Ser Tyr Ser Glu Glu Val
            300                 305                 310

Cys Arg Cys Val Pro Ser Tyr Trp Gln Arg Pro Gln Met Ser
    315                 320                 325
```

```
<210> SEQ ID NO 3
<211> LENGTH: 14
<212> TYPE: PRT
<213> ORGANISM: Homo sapiens
<220> FEATURE:
<221> NAME/KEY: SITE
<222> LOCATION: (2)
<223> OTHER INFORMATION: Xaa equals any amino acid
<220> FEATURE:
<221> NAME/KEY: SITE
<222> LOCATION: (5)..(7)
<223> OTHER INFORMATION: Xaa equals any amino acid
<220> FEATURE:
<221> NAME/KEY: SITE
<222> LOCATION: (10)
<223> OTHER INFORMATION: Xaa equals any amino acid

<400> SEQUENCE: 3

Pro Xaa Cys Val Xaa Xaa Xaa Arg Cys Xaa Gly Cys Cys Asn
  1               5                  10

<210> SEQ ID NO 4
<211> LENGTH: 18
<212> TYPE: DNA
<213> ORGANISM: Homo sapiens

<400> SEQUENCE: 4
atgcttccgg ctcgtatg                                             18

<210> SEQ ID NO 5
<211> LENGTH: 19
<212> TYPE: DNA
<213> ORGANISM: Homo sapiens

<400> SEQUENCE: 5
gggttttccc agtcacgac                                            19

<210> SEQ ID NO 6
<211> LENGTH: 21
<212> TYPE: DNA
<213> ORGANISM: Homo sapiens

<400> SEQUENCE: 6
ccacatggtt caggaaagac a                                         21

<210> SEQ ID NO 7
<211> LENGTH: 196
<212> TYPE: PRT
<213> ORGANISM: Homo sapiens
```

<400> SEQUENCE: 7

```
Met Arg Thr Leu Ala Cys Leu Leu Leu Gly Cys Gly Tyr Leu Ala
  1               5                  10                  15

His Val Leu Ala Glu Glu Ala Glu Ile Pro Arg Glu Val Ile Glu Arg
             20                  25                  30

Leu Ala Arg Ser Gln Ile His Ser Ile Arg Asp Leu Gln Arg Leu Leu
             35                  40                  45

Glu Ile Asp Ser Val Gly Ser Glu Asp Ser Leu Asp Thr Ser Leu Arg
 50                  55                  60

Ala His Gly Val His Ala Thr Lys His Val Pro Glu Lys Arg Pro Leu
 65                  70                  75                  80

Pro Ile Arg Arg Lys Arg Ser Ile Glu Glu Ala Val Pro Ala Val Cys
             85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
            115                 120                 125

Cys Thr Gly Cys Cys Asn Thr Ser Ser Val Lys Cys Gln Pro Ser Arg
130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
            165                 170                 175

Cys Ala Cys Ala Thr Thr Ser Leu Asn Pro Asp Tyr Arg Glu Glu Asp
            180                 185                 190

Thr Asp Val Arg
            195
```

<210> SEQ ID NO 8
<211> LENGTH: 241
<212> TYPE: PRT
<213> ORGANISM: Homo sapiens

<400> SEQUENCE: 8

```
Met Asn Arg Cys Trp Ala Leu Phe Leu Ser Leu Cys Cys Tyr Leu Arg
  1               5                  10                  15

Leu Val Ser Ala Glu Gly Asp Pro Ile Pro Glu Glu Leu Tyr Glu Met
             20                  25                  30

Leu Ser Asp His Ser Ile Arg Ser Phe Asp Asp Leu Gln Arg Leu Leu
             35                  40                  45

His Gly Asp Pro Gly Glu Glu Asp Gly Ala Glu Leu Asp Leu Asn Met
 50                  55                  60

Thr Arg Ser His Ser Gly Gly Glu Leu Glu Ser Leu Ala Arg Gly Arg
 65                  70                  75                  80

Arg Ser Leu Gly Ser Leu Thr Ile Ala Glu Pro Ala Met Ile Ala Glu
             85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
            115                 120                 125

Arg Cys Ser Gly Cys Cys Asn Asn Arg Asn Val Gln Cys Arg Pro Thr
130                 135                 140

Gln Val Gln Leu Arg Pro Val Gln Val Arg Lys Ile Glu Ile Val Arg
145                 150                 155                 160
```

-continued

```
Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
                180                 185                 190

Pro Gly Gly Ser Gln Glu Gln Arg Ala Lys Thr Pro Gln Thr Arg Val
                195                 200                 205

Thr Ile Arg Thr Val Arg Val Arg Arg Pro Pro Lys Gly Lys His Arg
        210                 215                 220

Lys Phe Lys His Thr His Asp Lys Thr Ala Leu Lys Glu Thr Leu Gly
225                 230                 235                 240

Ala

<210> SEQ ID NO 9
<211> LENGTH: 232
<212> TYPE: PRT
<213> ORGANISM: Homo sapiens

<400> SEQUENCE: 9

Met Asn Phe Leu Leu Ser Trp Val His Trp Ser Leu Ala Leu Leu Leu
  1               5                  10                  15

Tyr Leu His His Ala Lys Trp Ser Gln Ala Ala Pro Met Ala Glu Gly
                 20                  25                  30

Gly Gly Gln Asn His His Glu Val Val Lys Phe Met Asp Val Tyr Gln
                 35                  40                  45

Arg Ser Tyr Cys His Pro Ile Glu Thr Leu Val Asp Ile Phe Gln Glu
         50                  55                  60

Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
                115                 120                 125

Glu Cys Arg Pro Lys Lys Asp Arg Ala Arg Gln Glu Lys Lys Ser Val
        130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
                180                 185                 190

His Leu Phe Val Gln Asp Pro Gln Thr Cys Lys Cys Ser Cys Lys Asn
                195                 200                 205

Thr Asp Ser Arg Cys Lys Ala Arg Gln Leu Glu Lys Asn Glu Arg Thr
        210                 215                 220

Cys Arg Cys Asp Lys Pro Arg Arg
225                 230
```